United States Patent [19]

Reiss

[11] 4,320,086
[45] Mar. 16, 1982

[54] PAPER DEVICE FOR RAPID DETECTION OF COCAINE

[76] Inventor: Andre Reiss, 147 - 47 Village Rd., Jamaica, N.Y. 11435

[21] Appl. No.: 222,636

[22] Filed: Jan. 5, 1981

[51] Int. Cl.³ .................... G01N 31/22; G01N 33/52
[52] U.S. Cl. ................................. 422/56; 23/230 R; 23/230 B; 252/408
[58] Field of Search .................. 422/56; 23/230 B; 252/408

[56] References Cited

U.S. PATENT DOCUMENTS

| 3,799,741 | 3/1974 | Williams, Jr. | 23/230 B |
| 3,912,655 | 10/1975 | Shukla | 23/230 B X |
| 4,104,027 | 8/1978 | Carroll | 23/230 B |
| 4,110,078 | 8/1978 | Zelonis | 23/230 B X |

OTHER PUBLICATIONS

"Isolation and Identification of Drugs", E. G. C. Clarke, ed., pp. 267-268, The Pharmaceutical Press, London 1969.
William P. Butler, "Methods of Analysis", pp. 77-81, Internal Revenue Service, Publication No. 341.
F. Feigl, "Spot Tests in Organic Analysis", p. 147, Elsevier Publishing Co., New York, 1960.

*Primary Examiner*—Sidney Marantz

[57] ABSTRACT

A test device for detecting cocaine which comprises a wood fiber carrier and, incorporated therewith, a composition comprising cobalt thiocyanate and phosphotungstic acid. The test device is free of undesirable interference from procaine type compounds.

5 Claims, No Drawings

PAPER DEVICE FOR RAPID DETECTION OF COCAINE

BACKGROUND OF THE INVENTION

This invention relates to a test device and improved test composition for rapid detection of cocaine.

Cocaine and its salts have long been detected by contact with cobalt thiocyanate solution, an identifying blue color being formed. The standard Scott Test (L.J. Scott, Specific field test for cocaine, *Microgram* VI, 179, (1973)), used by the Customs Service, relies on systematic addition to a suspect substance of cobalt thiocyanate, hydrochloric acid, and chloroform. False positives from procaine type local anaesthetics, lack of portability, and difficulty in use are test liabilities.

BRIEF DESCRIPTION OF THE INVENTION

Relief from the above operational difficulties is the goal of this invention, and, in accordance with the invention, this goal is achieved in a test device comprising a bibulous carrier of wood fiber incorporating therein cobalt thiocyanate and phosphotungstic acid. The presence of cocaine compounds in a dry test sample is detected by a method which comprises contacting the test sample with the test device according to the invention, adding moisture, then observing resultant colorimetric response; blue for cocaine; green for procaine type interferents.

DETAILED DESCRIPTION OF THE INVENTION

In accordance with the invention, acidified wood fiber has been found to develop a strong yellow to orange color with many of the interferents troubling cobalt thiocyanate based detection methods for cocaine and its compounds. Added to the blue color formed with cobalt thiocyanate, the yellow interferent color will appear green to the eye and easily discernible from cocaine which does not react colorimetrically with wood fiber.

A source rich in wood fiber is common newsprint paper, allowing its practical use as a bibulous carrier. Phosphotungstic acid is utilized as a color intensifying agent for the newsprint and as a precipitant of reactive test samples on the paper surface, thereby allowing clear color development.

Both cobalt thiocyanate and phosphotungstic acid may be obtained as preparative materials with variety in their water of hydration. In accordance with the invention, chemical water of hydration is specified, but not limited to: cobalt thiocyanate, $Co(SCN)_2.3H_2O$, and phosphotungstic acid, $24WO_3.2H_3PO_4.48H_2O$. For preparation of material with other water of hydration, one skilled in the art may easily make the proper weight adjustments.

The cocaine test device is prepared by impregnating paper rich in wood fiber, such as Grumbacher newsprint, with a solution containing the following components, desirably in the proportions by weight indicated:

Cobalt thiocyanate . . . 2–6%
Phosphotungstic acid . . . 1–5%

An aqueous solution of a relatively low boiling organic solvent, such as methanol or ethanol, ranging from 30–60% alcohol, is most advantageous for easy evaporation of solvent.

In order to use the test device, a few milligrams of test material are rubbed across the dry, blue test paper with a wetted finger or other suitable tool. The test device will react as follows: (1) the paper will turn only pink from reaction of cobalt thiocyanate with water; (2) the paper will turn pink with green streaks, the green streaks identifying a procaine type interferent; (3) the paper will turn pink with blue streaks, the blue streaks identifying cocaine or its compounds.

The following example will illustrate the invention, but is not intended to limit it thereby.

EXAMPLE 4 g cobalt thiocyanate and 2 g phosphotungstic acid are dissolved in 50 ml water, then 50 ml anhydrous methanol are therein mixed. Sheets of newsprint (Grumbacher) are soaked in the solution, drained, then dried in air and out to suitable size. The dry paper is used as outlined above.

I claim:

1. A test device for the colorimetric determination of cocaine or its compounds, said device comprising a bibulous carrier incorporating a dry residue of a solution comprising cobalt thiocyanate and phosphotungstic acid.

2. The device of claim 1 in which the bibulous carrier comprises wood fiber.

3. The device of claim 1 in which the bibulous carrier comprises a substance rich in wood fiber.

4. The device of claim 1 in which the bibulous carrier comprises newsprint paper.

5. A process for preparing the test device according to claim 1 comprising impregnating the bibulous carrier with an impregnating solution containing by weight 2–6% cobalt thiocyanate and 1–5% phosphotungstic acid.

* * * * *